United States Patent
Mason et al.

(10) Patent No.: US 10,405,553 B1
(45) Date of Patent: Sep. 10, 2019

(54) ANTIMICROBIAL ARTICLES AND COMPOUNDS THEREFOR

(71) Applicants: Joseph E. Mason, Belews Creek, NC (US); Dennis Victor Neigel, Salisbury, NC (US)

(72) Inventors: Joseph E. Mason, Belews Creek, NC (US); Dennis Victor Neigel, Salisbury, NC (US)

(73) Assignee: Indusco, Ltd., Greensboro, NC (US)

( * ) Notice: Subject to any disclaimer, the term of this patent is extended or adjusted under 35 U.S.C. 154(b) by 83 days.

(21) Appl. No.: 15/453,108

(22) Filed: Mar. 8, 2017

Related U.S. Application Data

(63) Continuation of application No. 14/680,689, filed on Apr. 7, 2015, now Pat. No. 9,624,384.

(51) Int. Cl.
```
A01N 25/22    (2006.01)
A01N 55/00    (2006.01)
A01N 25/04    (2006.01)
A01N 65/28    (2009.01)
A01N 65/22    (2009.01)
A01N 65/36    (2009.01)
A01N 65/06    (2009.01)
```

(52) U.S. Cl.
CPC ............ *A01N 55/00* (2013.01); *A01N 25/04* (2013.01); *A01N 25/22* (2013.01); *A01N 65/06* (2013.01); *A01N 65/22* (2013.01); *A01N 65/28* (2013.01); *A01N 65/36* (2013.01)

(58) Field of Classification Search
CPC ...................................................... A01N 25/22
See application file for complete search history.

(56) References Cited

U.S. PATENT DOCUMENTS

| | | |
|---|---|---|
| 2,005,008 A | 6/1935 | Schaer |
| 3,560,385 A | 2/1971 | Roth |
| 3,730,701 A | 5/1973 | Isquith et al. |
| 3,794,736 A | 2/1974 | Abbott et al. |
| 3,860,709 A | 1/1975 | Abbott et al. |
| 3,865,728 A | 2/1975 | Abbott et al. |
| 4,005,025 A | 1/1977 | Kinstedt |
| 4,005,028 A | 1/1977 | Heckert et al. |
| 4,005,030 A | 1/1977 | Heckert et al. |
| 4,161,518 A | 7/1979 | Wen et al. |
| 4,282,366 A | 8/1981 | Eudy |
| 4,361,273 A | 11/1982 | Levine et al. |
| 4,393,378 A | 7/1983 | Danielsen et al. |
| 4,394,378 A | 7/1983 | Klein |
| 4,406,892 A | 9/1983 | Eudy |
| 4,421,796 A | 12/1983 | Burril et al. |
| 4,467,013 A | 8/1984 | Baldwin |
| 4,564,456 A | 1/1986 | Homan |
| 4,567,039 A | 1/1986 | Stadnick et al. |
| 4,615,882 A | 10/1986 | Stockel |
| 4,682,992 A | 7/1987 | Fuchs |
| 4,781,974 A | 11/1988 | Bouchette et al. |
| 4,797,420 A | 1/1989 | Bryant |
| 4,842,766 A | 6/1989 | Blehm et al. |
| 4,847,088 A | 7/1989 | Blank |
| 4,908,355 A | 3/1990 | Gettings et al. |
| 5,013,459 A | 5/1991 | Gettings et al. |
| 5,411,585 A | 5/1995 | Avery et al. |
| 5,468,725 A | 11/1995 | Guenin et al. |
| 5,660,891 A | 8/1997 | Kenyon et al. |
| 5,719,114 A | 2/1998 | Zocchi et al. |
| 5,954,863 A | 9/1999 | Loveless et al. |
| 5,954,869 A | 9/1999 | Elfersy et al. |
| 5,959,014 A | 9/1999 | Liebeskind et al. |
| 6,110,474 A | 8/2000 | Roman |
| 6,235,298 B1 | 5/2001 | Naser et al. |
| 6,376,696 B1 | 4/2002 | Raab et al. |
| 6,384,003 B1 | 5/2002 | Julemont |
| 6,451,755 B1 | 9/2002 | Norman |
| 6,613,755 B2 | 9/2003 | Peterson et al. |
| 6,632,805 B1 | 10/2003 | Liebeskind et al. |
| 8,541,610 B2 | 9/2013 | Taralp |
| 8,921,303 B1 | 12/2014 | Lull et al. |
| 9,089,138 B2 | 7/2015 | Higgins et al. |

(Continued)

FOREIGN PATENT DOCUMENTS

| | | |
|---|---|---|
| CA | 1217004 | 1/1987 |
| EP | 2460409 | 6/2012 |

(Continued)

OTHER PUBLICATIONS

Prabuseenivasan, S., et al. "In vitro antibacterial activity of some plant essential oils." BMC Complementary and Alternative Medicine. (Nov. 30, 2006), vol. 6, Issue 39, pp. 1-8 of 8. (Year: 2006).*
Traber, M.G., et al. "Vitamen E: function and metabolism," FASEB Journal. (Jul. 1999), vol. 13, pp. 1145-1155.
Sabine, J.R., et al. "Laboratory Evaluation of some Marine Plants on South Australian Beaches." J. Agric. Sci. Technol. (2001), vol. 3: pp. 91-100. (2001).
Sabine, J.R., et al. "Laboratory Evaluation of some Marine Plants on South Australian Beaches." J. Agric. Sci. Technol. (2001), vol. 3: pp. 91-100.
A. J. Asquith; Surface-Bonded Antimicrobial Activity of an Organosilicon luatemary Ammonium Chloride; Copyright 1973 American Society of Microbiology; Applied Microbiology, Dec. 1972 p. 859-863, vol. 24, No. 6.

(Continued)

*Primary Examiner* — Noble E Jarrell
*Assistant Examiner* — John S Kenyon
(74) *Attorney, Agent, or Firm* — Tuggle Duggins P.A.; Blake Hurt

(57) ABSTRACT

Antimicrobial treated articles and compounds. The article includes a substrate and an antimicrobial mixture of an effective amount of at least one antimicrobial silanol quaternary ammonium compound, at least one essential oil and the balance water. In one embodiment, the antimicrobial mixture is forming in a reaction medium for mixing the at least one antimicrobial silanol quaternary ammonium compound and the at least one essential oil together prior to treating the substrate.

7 Claims, 7 Drawing Sheets

(56) References Cited

U.S. PATENT DOCUMENTS

| | | |
|---|---|---|
| 2003/0114345 A1 | 6/2003 | Leonard et al. |
| 2005/0008613 A1 | 1/2005 | Peterson et al. |
| 2006/0115440 A1 | 6/2006 | Arata et al. |
| 2006/0193816 A1 | 8/2006 | Elfersy et al. |
| 2007/0021383 A1 | 1/2007 | Loder |
| 2007/0161526 A1 | 7/2007 | Vlad et al. |
| 2007/0237901 A1 | 10/2007 | Moses et al. |
| 2008/0181862 A1 | 7/2008 | Chisholm et al. |
| 2010/0028462 A1* | 2/2010 | Bolkan ............... A01N 55/00 424/717 |
| 2010/0167613 A1 | 7/2010 | Higgins et al. |
| 2011/0233810 A1 | 9/2011 | Neigel et al. |
| 2012/0149623 A1 | 6/2012 | Li et al. |
| 2013/0030207 A1 | 1/2013 | Taralp |
| 2015/0182446 A1 | 7/2015 | Fenyvesi et al. |

FOREIGN PATENT DOCUMENTS

| | | |
|---|---|---|
| GB | 1386876 | 3/1975 |
| WO | 1997-041729 | 11/1997 |
| WO | 2000-078770 | 12/2000 |
| WO | 2007-133934 | 11/2007 |
| WO | 2011-119237 | 9/2011 |
| WO | WO 2011119237 | 9/2011 |
| WO | 2011-123623 | 10/2011 |
| WO | 2013-075921 | 5/2013 |
| WO | 2015-002786 | 1/2015 |
| WO | WO 2015002786 | 1/2015 |
| WO | 2016-164545 | 10/2016 |
| WO | 2018-048552 | 3/2018 |

OTHER PUBLICATIONS

Traber, M.G., et al. "Vitamin E: function and metabolism," FASEB Journal. (Jul. 1999), vol. 13, pp. 1145-1155.

Google Search—jp 2091008—related patents, (the second being U.S. Pat. No. 8,541,610, No. 42 on this list).

International Search Report for PCT/US2016/026387 dated Jul. 15, 2016.

International Search Report for PCT/US2017/045857 dated Nov. 6, 2017.

* cited by examiner

ANTIMICROBIAL ARTICLES AND COMPOUNDS THEREFOR

This is a continuation of and claims benefits under prior application Ser. No. 14/680,689, filed 7 Apr. 2015, now U.S. Pat. No. 9,624,384 which is incorporated by reference in its entirety herein.

FIELD OF THE INVENTION

The present inventions relate generally to improved antimicrobial articles and compounds, and more specifically, to water solubilized silanol quaternary ammonium compounds that are stabilized using botanicals such as essential oils and extracts.

DESCRIPTION OF THE PRIOR ART AND OBJECTIVES OF THE INVENTION

A biocide is any substance that kills microorganisms such as bacteria, molds, algae, fungi or viruses. A biostatic is any substance that inhibits the growth of these organisms. The collective group is called antimicrobials. People have been utilizing antimicrobials, commonly called preservatives, since they first discovered a need to extend the useful life of their food as well as their possessions. Sea salt may have been the first antimicrobial used to preserve food. The mummification techniques employed by early Egyptians used to preserve the human and animal body used salts and a variety of resins. These preservatives were thought to possess magical powers, as well as the ability to install qualities of eternal life.

The existence of microorganisms in nature was discovered in the late 1600s with the invention of the microscope. As early as 1705, mercuric chloride was used to preserve ships' planking against shipworm. It was not until the 19th century discoveries by Pasteur, Gram and others that the causative agents of microbiological deterioration were understood, although use of antimicrobials in a cause and effect relationship with microorganisms is still less than a century old.

Certain silanol quaternary ammonium compounds ("SQACs") possess bacteriostatic, fungistatic and algaestatic and/or bactericidal, fungicidal and algaecidal properties. For example, 3-(trimethoxysilyl)propyl octadecyldimethyl ammonium chloride is a commercial antimicrobial product marketed by Dow Corning as "BIOGUARD Q 9-5700". A number of other organosilicon amines and salts also exhibit antimicrobial activity.

Reactive silanols are able to bond with a variety of target surfaces because they form a covalent bond with any surface containing oxygen, nitrogen or carbon in any form. For example, hydroxides or oxides on the surfaces of metals (including stainless steel) will thin' a durable bond. In addition, silanol groups will homopolymerize via a condensation mechanism to form a durable, 3 dimensional crosslinked polymer matrix. Reactive silanols are therefore able to bond with surfaces such as plastic, metal, fabric, tile, masonry, vinyl, wood, painted surfaces and human skin.

When silanols are modified with biocidal adjuncts in the form of alkyl quaternary ammonium groups, and the silanols are fixed onto a surface, the active biocidal sites become fixed too. The films created are extremely thin, between 15 nm and 180 nm, and therefore the original physical properties of the surface are little affected.

Silanols having biocidal adjuncts typically exhibit a mechanism of action whereby bacteria arriving on a treated surface will assimilate the biocidal adjunct's hydrocarbon, and the positively charged nitrogen atom will affect the electrical equilibrium of the cell. More specifically, the nitrogen atom disrupts the porin channels and/or outer protein layers, causing cell death.

The fixed nature of the biocide is important where toxicity, taint and other organoleptic aspects are of concern. This bactericidal surface treatment is not removed by normal cleaning procedures. In fact, it is important to maintain the normal cleaning regime in order to 'refresh' biocidal surface. The thinness of the film enables application in areas where optical properties important such as treatment of contact lenses. Silanols with biocidal adjuncts have been used in the treatment of bed sheets, hospital garments, curtains, floor and wall materials, air filtration systems, medical devices, bandages, surgical instruments and implants, and to prevent biofilm growth on catheters, stints, contact lenses and endotracheal tubes.

Based toxicity information, the EPA concluded that there are no endpoints of concern for repeated oral or dermal exposure to the trimethoxysilyl quats. This conclusion was based on low toxicity observed in acute, subchronic and developmental studies conducted with the trimethoxysilyl quat compounds. They further concluded that there are no concerns for carcinogenicity for the trimethoxysilyl quats based on the results of the mutagenicity studies and the lack of any systemic toxicity in the toxicity database.

Based on hydrolysis data, the EPA has concluded that trimethoxysilyl quats are soluble but not stable in water. They stated that due the instability of the compounds and their formation of an insoluble silane degradate, that the trimethoxysilyl quats are not expected to contaminate surface or ground water due to rapid degradation by hydrolysis.

While aqueous SQACs have a tremendous amount of potential as antimicrobials, there are significant shortcomings. They are very unstable and have a short shelf life. For example, premature sedimentation of polysilsesquioxane-type polymers occurs in even low aqueous concentrations. Also, premature polymerization causes unwanted solution viscosity, thereby complicating conventional coating methods.

A variety of strategies have been employed in order to extend the storage life of aqueous SQACs. Examples include introducing surfactant additives, to coordinate the free silanol ends with stabilizers such as simple sugars and other multiple hydroxyl group molecules; coordinating and associating said quaternary organosilane hydrolysates with hydrophilic polymers; incorporating non-aqueous solvents such as the toxic methanol and methyl or butyl cellosolve; using alternative aqueous/organic systems; and combinations thereof. In some cases, pH adjustments have been used to maximize the benefits imparted by a stabilizer. These strategies all have shortcomings including undesirably creating a hydrophilic toxicity and cost.

It is desirable that the aqueous medium contains additives and components that eliminate or decrease the premature homopolymerization of the hydrolyzed silanol groups, thereby increasing storage stability. It is desirable that the aqueous medium contains additives and components that eliminate or decrease unwanted increases in viscosity arising from premature homopolymerization. It is desirable that the aqueous medium contains additives and components that eliminate or decrease unwanted precipitation arising from premature homopolymerization. is also desirable that the aqueous medium contains additives and components that impart a pleasant scent, maintain solution clarity, improve performance of the underlying SQAC, and protect the composition against aqueous mold growth. It is desirable that the additives will evaporate completely during the coating and curing operation, thus allowing the generation of a high degree of homopolymer crosslinking of the silanol groups, thereby providing a highly water and solvent insoluble coating on the substrate. It is desirable that the additives are not and that they do not alter the cationic charge density of the SQAC. It is also desirable that the additives and components are environmentally friendly.

In short, it is desirable to have antimicrobial compounds and articles having the following characteristics: 1) Low Toxicity; 2) Low Flammability; 3) Excellent stabilization of aqueous SQACs; 4) Pleasant scent; 5) Volatility (little or no incorporation of the stabilizer into the cured film); 6) Antimicrobial Activity; and 7) Obtained from a renewable resource.

Thus, there is a need for antimicrobial treated articles and compounds which are effective in use while, at the same time, remain stable for long periods of time after preparation.

SUMMARY OF THE INVENTION

The present inventions are directed to an antimicrobial treated article, the article includes a substrate treated with an antimicrobial mixture of an effective amount of at least one antimicrobial silanol quaternary ammonium compound, at least one essential oil and the balance water. In one embodiment, the antimicrobial mixture is forming in a reaction medium for mixing the at least one antimicrobial silanol quaternary ammonium compound and the at least one essential oil together prior to treating the substrate.

The at least one antimicrobial silanol quaternary ammonium compound may be selected from 3-(trimethoxysilyl) propyl-N-octadecyl-N,N-dimethyl ammonium chloride, 3-3-(trimethoxysilyl) propyl-N-tetradecyl-N,N-dimethyl ammonium chloride and 3-3-(trihydroxysilyl) propyl-N-octadecyl-N,N-dimethyl ammonium chloride and mixtures thereof. In one embodiment, the antimicrobial silanol quaternary ammonium compound is 3-3-(trimethoxysilyl) propyl-N-octadecyl-N,N-dimethyl ammonium chloride.

The at least one antimicrobial silanol quaternary ammonium compound may be between about 0.1 wt. % and about 10 wt. % of the mixture. In one embodiment, the at least one antimicrobial silanol quaternary ammonium compound is between about 0.1 wt. % and about 1 wt. % of the mixture. In another embodiment, the at least one antimicrobial silanol quaternary ammonium compound is greater than about 0.2 wt. % of the mixture.

Also, the ratio of the weight of the at least one volatile essential oil to the weight of the at least one antimicrobial silanol quaternary ammonium compound is greater than about 0.15. In one embodiment, the ratio of the weight of the at least one volatile essential oil to the weight of the at least one antimicrobial silanol quaternary ammonium compound is between about 0.2 and about 0.5. In another embodiment, the ratio of the weight of the at least one volatile essential oil to the weight of the at least one antimicrobial silanol quaternary ammonium compound is about 0.3.

The volatile essential oil may be a mixture of more than one essential oils. In one embodiment, the essential oil is selected from the group consisting of tea tree oil, peppermint oil, thyme oil, grapefruit oil, lemon oil, lime oil, orange oil, tangerine oil, cedarwood oil, pine oil, and mixtures thereof, and the extract is orange peel extract d-limonene.

Also, the reaction medium may be a volatile organic reaction medium. In one embodiment, the volatile organic reaction medium is selected from a group consisting of aliphatic compounds. In one embodiment, the volatile organic reaction medium is an alcohol. In another embodiment, the alcohol is methanol.

Substrates of the present invention may be organic or inorganic, in a variety of forms as textiles, clothing articles, and building materials. Antimicrobial mixtures may be applied to substrates in a variety of methods including spraying and dipping.

Accordingly, one aspect of the present inventions is to provide an antimicrobial treated article, the article including (a) a substrate; and (b) an antimicrobial mixture for treating a substrate of an effective amount of at least one antimicrobial silanol quaternary ammonium compound and at least one essential oil.

Another aspect of the present inventions is to provide an antimicrobial mixture for treating a substrate, the antimicrobial mixture including (a) at least one antimicrobial silanol quaternary ammonium compound; (b) at least one volatile essential oil; and (c) the balance water.

Still another aspect of the present inventions is to provide an antimicrobial treated article, the article including (a) a substrate; and (b) an antimicrobial mixture for treating a substrate of (i) an effective amount of at least one antimicrobial silanol quaternary ammonium compound, (ii) at least one essential oil and (iii) the balance water wherein the antimicrobial mixture is forming in a reaction medium for mixing the at least one antimicrobial silanol quaternary ammonium compound and the at least one essential oil together prior to treating the substrate.

These and other aspects of the present inventions will become apparent to those skilled in the art after a reading of the following description of the preferred embodiment when considered with the drawings.

DETAILED DESCRIPTION OF THE PREFERRED EMBODIMENT AND OPERATION OF THE INVENTION

Figure 1:
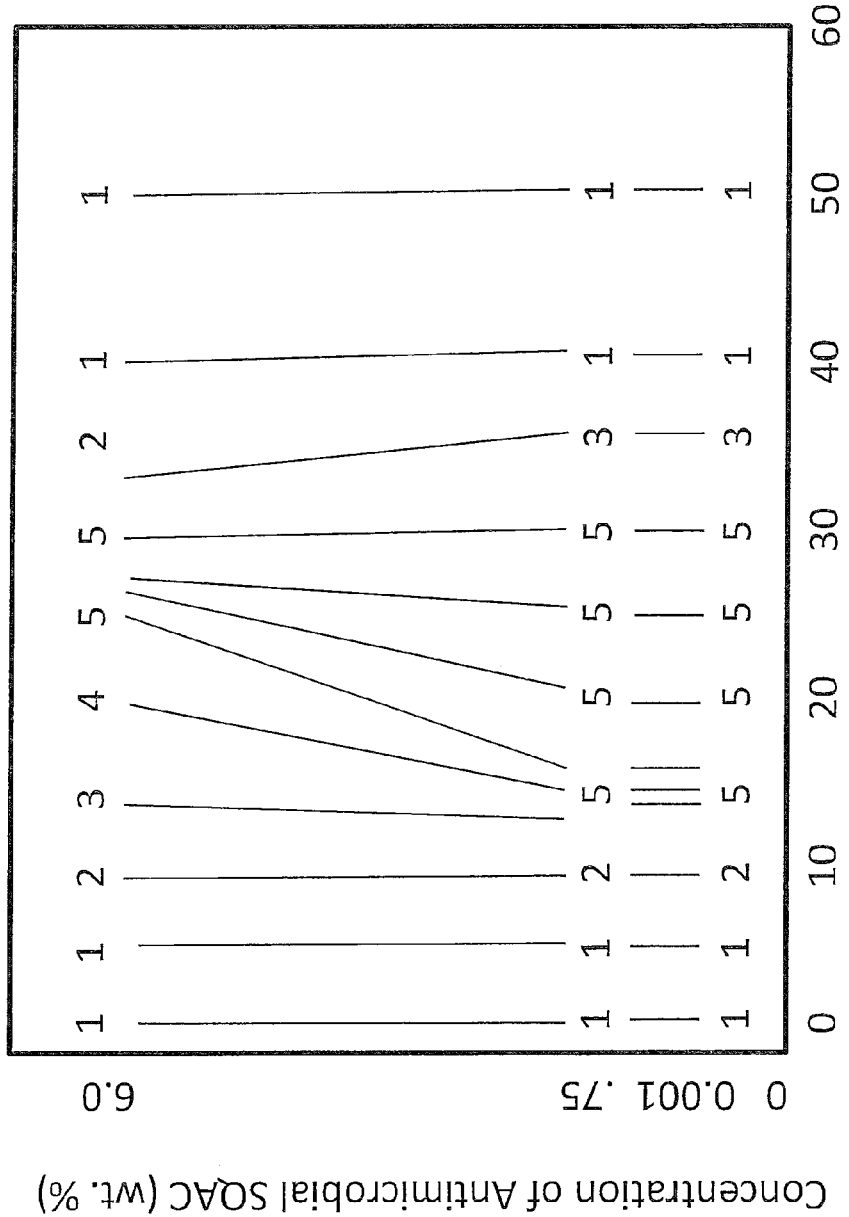
FIG. 1 is a graphical representation of the expected overall desirability of microbial compositions prepared according to the present inventions as a function of the concentration of volatile botanical and the concentration of silanol quaternary ammonium compound.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

As used herein, the following terms apply:

"Botanical" or "Phytochemical" is a substance derived from a plant, such as an essential oil or extract.

"Stable" shall mean no phase separation, precipitation, turbidity values of <40 NTU and viscosity of <50 cPs at 6% active SQAC in water for at least 3 months at 25 C.

"SQAC" is a silanol quaternary ammonium compound. Preferred examples discussed herein are designated as SQAC #1-3.

"SQAC #1" is 3-(trimethoxysilyl) propyl-N-octadecyl-N,N-dimethyl ammonium chloride.

"SQAC #2" is 3-(trimethoxysilyl) propyl-N-tetradecyl-N,N-dimethyl ammonium chloride.

"SQAC #3" is 3-(trihydroxysilyl) propyl-N-octadecyl-N,N-dimethyl ammonium chloride.

SQAC #1 is commercially available from Indusco, Ltd located in Greensboro, N.C. as Bioshield 7200 and sold as a concentrated solution of the active ingredient in anhydrous methanol A similar product is available from both Dow Corning and Microban International and others. Of the three selected SQAC compounds, SQAC #1 is one acceptable compound for demonstrating the process of these inventions due to its high sales volume and popularity of use as an antimicrobial coating on a myriad of substrates.

Following is a non-exhaustive list of antimicrobial phytochemical plant species whose botanicals, including essential oils and extracts, may be used in these inventions: *Jasonia candicans* (sesquiterpenes, lactones); *Polygonum flaccidum* (flavone and alpha santalene derivatives); *Acalypha wikesiana* (extracts); *Pavetta owariensis* (procyanidins); *Plectranthus hereroensis* (diterpenoids, diterpenes); Moss (Dicranin extract); *Cannabis sativa* (extract); *Gloiosiphonia* spp. (gloiosiphones); *Laminaceae* spp. (extract); *Securidaca* spp. (extract); spp. (extract); *Hyptis umbrose* (umbrosone); *Asclepias syriaca* (milkweed extract); *Tagetes tenuifolia* (thiophene); *Calophyllum inophylloide* (flavonoids); *Tanacetum densum* lactones, triterpenoids); *Neorautanenia mitis* (extract); *Premna schimper* (diterpene); *Premna oligotricha* (sesquiterpenes); *Premna oligotricha* (diterpenes); *Jasonia candicans* (essential oils); oils); *Visnea mocanera* (beta-sitosterol, triterpenic betulinic acid, ursolic acid, plantanic acid); *Asteraceae* spp. (terthiophenes and polyynes); *Petalostemum purpureum* (extract); *Camelia sinensis* (catechin); *Helichrysum picardii* (flavonoids); *Helichrysum italicum* (flavonoids); *Corydalis pallida* (protoberberine alkloids); *Shiraia bambusicola* (perylenequinones); *Fraxinum omus* (hydroxycoumarins); *Podocarpus nagi* (totarol and nortiterpene dilactones); *Heterotheca inuloides* (sesquiterpenoids); *Pelargonium* spp. (essential oils); *Piper sarmentosum* (phenylpropanoids); *Allium* spp. (extract); *Juniperus procera* (diterpenes); *Achillea conferta* (flavonoids, flavones, sesquiterpenoid lactones); (chromenes, prenylated benzoic acid); *Rhamnaceae* spp. (cyclopeptide alkaloids); *Buddleja globosa* (verbascoside); *Cephalocereus senilis* (phytoalexin aurone); *Salvia albocaerulea* (diterpene); *Gomphrena martiana* and *Gomphrena boliviana* (extracts); *Paepalanthus* spp. (vioxanthin); *Helichrysum stoechas* and *Helichrysum crispum* (extracts); *Achillea ptarmica* (trans-pinocarveyl hydroperoxides); *Dehaasia incrassata* (alkaloids); *Asteraceae* spp. (extracts); *Arctotis auriculate* (extracts); *Eriocephalus africanus* (extracts): *Felicia erigeroides* (extracts); *Hemerocallis fulva* (phytosterols, fatty acid esters); *Psoralea juncea* (plicatin B); *Pluchea symphytifolia* (caffeic acid esters); *Tovomitopsis psychotrifolia* (Vitamin E derivative), *Celosia argentea* (triterpenoid saponins and flavonoids); *Azadirachta indica* (tetranortriterpenoid, mahmoodin, protolimonoids, naheedin); *Moracea* spp. (coumarins); *Hypericum erectum* (phloroglucinol derivatives); *Podospora appendiculate* (Appenolides A, B, & C, furanones); *Artemisia princeps* var. *orientalis, Artemisia capillaris, Artemisia mexicana* and *Artemisia scoparia* (extract); Paddy malt (mash extract); *Kigelia pinnata* (extract); *Acalypha wilkesiana* (extract); seaweeds, seagrass and lemongrass (essential oils); *Borrieria latifolia, Borreria setidens, Hedyotis diffusa), Hedyotis nudicaulis, Morinda elliptica, Morinda umbellata, Sida rhombifolia,* and *Vitex ovata* (extracts); *Tabebuia impetiginosa, Achyrocline* spp., *Larrea divaricata, Rosa borboniana, Punica granatum, Psidium guineense, Lithrea ternifolia* (extracts); *Lepechinia caulescens, Lepidium virginicum* and *Tanacetum parthenium* (extracts); *Talaromyces flavus* (extracts); *Daucus carota* (extract); *Flabellia petiolata, Caulerpa prolifera, Halimeda tuna, Corallina elongata, Lithophyllum lichenoides, Phyllophora crispa, Cystoseira* spp., *Halopteris* spp., *Codium* spp., *Valonia utricularis, Posidonia oceanica, Zostera noltii* and *Cymodocea nodosa* (extracts); *Centauraea orientalis, Diospyros khaki, Sida hermaphrodita, Forsythia intermedia, Scutellaria polydon, Eugenia malaccensis* and *Eugenia jambolana* (extracts); *Fritillaria* L. spp. (ebeinone, steroidal alkaloids); *Kigelia pinnata, pellucida, Populus nigra, Populus balsamifera* and *Populus deltoides* (extracts); *Melaleuca alternifolia* (essential oil); *Elfvingia applanata* (naringenin); *Ficus sycomorus*, grapefruit seed, Garlic, Allicin, Peat, *Strophanthus hispidus, Secamone afzeli, Mitracarpus scaberi, Entada abyssinjca, Terminalia spinosa, Harrisonia abyssinica, Ximinea caffra, Azadirachta indica, Spilanthes mauritiana, Terminalia spinosa* (extracts); Cyanobacteria (ambigols A and B, ipanazole); coffee (extract); *Sporochnus latifolia, Pelargonium xhortorum, Rhus glabra* and *Lindera benzoin* (extracts); *Striga densiflora, Striga orobanchioides, Striga lutea, Pistacia* L., *Mitracarpus villosus, Bixa orellana, Bridelia ferruginea, Alpinia katsumadai, Alpinia officinarum, Artemisia capilaris, Casia obtusifolia, Dendrobium Epimedium grandiflorum, Glycyrrhiza glabra, Lithosperum erythrorhizon, Magnolia obovata, Morus bonbycis, Natopterygii incisium, Polygonum multiflorum, Prunus mume, Rheum palmatum, Ricinus communis, Sophora flavescens, Swertia japonica*, black pepper, rosemary, red pepper, *lsopyrum thalictroides, Calotropis procera, Chrysanthemum* spp., *Holarrhena antidysenterica, Lunularia crusiata, Dumertiera hirsuta, Exotmotheca tuberifera*, and liverwort (extracts); *Filipendula ulmaria, Salix glauca, Usnea filipendula, Clkadina arbuscula* (salicylic compounds); *Tanacetum parthenium, Thymus capitatus*, and *Elfingia applanata* (extracts); *Fraxinus ornus* (hydroxycoumarins, esculin, esculetin, fraxin, and fraxetin); *Zizyphus nummularia*, LONGO VITAL, *Pelargonium* spp., *Scaevola sericea, Psychotria hawaiiensis, Pipturus albidis, Aleurites moluccana, Solanum niger, Piper methysticum, Barringtonia asiatica, Adansonia digitata, Harungana madagascariensis, Jacaranda mimosaefolia, Erythroxylum catauba, Bidens pilosa, Lemna minor, Potamogeton* spp., *Nasturtium officinale, Apium nodiflorum, Agaricus subrutilescens, Amanita virosa, Amanita pantherina, Lycoperdon perlatum, Psidium guajava, Averrhoa carambola, musa sapientum, Caric papaya, Passiflora edulis, Lansium domesticum* and *Baccaurea motleyana* (extracts); horse radish, celandine grass, bur marigold and yarrow grass (extracts); *Abuta grandifola, Cyperus articulatus, Gnaphalium spicatum, Pothomorphe peltata, Ficus sycomorus, Ficus Benjamina, Ficus bengalensis, Ficus religiosa, Alchornea*

*cordifolia, Bridelia feruginea, Eucalyptus citriodora, Hymenocardia acida, Maprounea africana, Monachora arbuscula, Tedania ignis, Arenosclera* spp., *Amphimedon viridis, Polymastia janeirensis, fulva, Pseudaxinella lunaecharta, Nelumbium speciosum* and *Mycale arenosa* (extracts); cloves (eugenol acetate an iso-eugenol); *Chrysthanemum boreale* (sesquiterpenoid lactones); *Eucalyptus globolus, Punica granatum, Bocconia arborea, Syzygium brazzavillense, Syzygium guineense, Carthamus tinctorius*), *Ginkgo biloba, Mosla chinensis, Salvia officinalis*, and *Cinnamomum cassia* (extracts); *Cryptolepis sanguinolenta* (alkaloids, cryptolepine); *Chelidonium majus* (alkaloids, berberine, coptisine); *Vitex agnus-castus* (extract); *Cladonia substellata* (usnic acid); *Fuligo septica, Tubifera microsperma* (extract); *Mundulea monantha, Tephrosia linearis* (flavonoids); *Lpomoea fistulosa* (extract); *Pimenta dioica* (essential oils); *Ratibida latipalearis, Teloxys graveolens, Dodonaea viscosa, Hypericum calycinum, Hyptis albida, Hyptis pectinata, Hyptis suaveolens* and *Hyptis verticillata* (extracts); *Asteriscus graveolones* (bisabolone hydroperoxides); *Derris scandens, Alnus rubra*, Araliaceae family (extracts); *Vinca rosea*, Australian tea tree oil, peppermint oil, sage oil, thyme oil, thymol, grapefruit oil, lemon oil, lime oil, orange oil, tangerine oil, cedarwood oil, pine oil and d-limonene, eugenol and *Thuja* (extracts); *Anacardium occidentale* (phenolic lipids); *Oidiodendron tenuissimum* (extract); nilotica and *Acacia farnesiana* (polyphenol, tannin); *Teminalia alata* and *Mallotus phillipinensis* (extracts); *Piectranthus grandidentatus* (abientane diterpenoids); *Pumica granatum* and *Datura metel* (extracts); tea, *Agave lecheguilla, Chamaesyce hirta, Baccharis glutinosa* and *Larrea tridentata* (extracts); *Camelia sinensis* and *Euphorbia hirta* (theaflavin, polyphenon 60); *Tabemaemontana pandacaqui, Yucca shidigera, Hemistepa lyrata, Yougia japonica, Prunella vulgaris, Lamium amplexicaule, Juniperus chinensis, lxeris dentata, Gnaphalium affine, Chelidonium majus, Spirea prunifolia, Erythronium japonicum, Taxus wallichiana, Ganoderma lucidum Drava nemorosa, Youngia capillaris, Equisetum arvense, Australiam Lavender*, Black Seed, *Catuaba casca, Cineole, Damiana, Dicranum scoparium, Eucalyptus* oil, Ginger, and seed (extracts); Neem seed, bark, and leaf extract; Neem oil; New Zealand Manuka extract; *Nicotiana tabacum* extract; olive leaf extract; a-pinene and b-pinene extracts; Rhubarb root *Syringa vulgaris* extract.

For purposes of demonstrating the processes of these inventions, preferred essential oils that have biocidal activity and form crystal clear microemulsions with aqueous SQACs are the essential oils of tea tree, peppermint, thyme, grapefruit, lemon, lime, orange, tangerine, cedarwood and pine and orange peel extract d-limonene.

The processes of the present inventions produce novel, crystal clear, viscosity stable, oil-oil-in-water microemulsions using SQACs, phytochemical extracts or essential oils, and distilled or deionized water. Compositions of the present invention are considered stable in water. Microemulsion technology has been in existence for many years. In fact, many commercial microemulsion products are found in the marketplace including floor polishes and cleaners, personal care products, pesticide delivery systems, cutting oils and drug delivery systems. Microemulsions are crystal clear because the micellar particle size is too small to scatter visible light. The IUPAC definition of microemulsion is "a dispersion of water, oil and surfactant(s) is an isotropic and thermodynamically stable system with dispersed domain diameter varying approximately from 1 to 100 nm, usually 10 to 50 nm." The aqueous phase may contain salts or other ingredients such as polar solvents, and the oil may be a complex mixture of organic compounds. In contrast to ordinary, white macroemulsions that usually require high shear conditions to form, microemulsions form upon simple mixing of the components, without the for high-energy homogenization. Also, microemulsions of the present inventions are stable against phase separation.

SQAC is an active ingredient that produces durable antimicrobial films when cured. SQAC also does double duty as a suitable surfactant when used alone. Unexpectedly, SQAC is able to form a microemulsion with phytochemical essential oils and extracts. Such microemulsions need only standard mixing requirements such as those found in low speed mixing vessels, not high shear equipment such as various types of high speed or high-pressure homogenizers. These microemulsions have been developed on lab scale using only the shear of low speed magnetic stirring bar mixing.

It has also been found according to the present inventions that when preparing these microemulsions, order of addition is quite important. The SQAC is first to be added to the mixing vessel as a concentrated solution in the reaction solvent, followed by adding the essential oil or extract, which dissolves in the concentrated SQAC to form a low viscosity, easily mixable, clear solution. The addition of the essential oil or extract will lower the temperature at which partial insolubility of the SQAC occurs, similarly to what would be expected if more reaction solvent was added. Mixtures of SQAC and essential oil or extract have been stored at room temperature for several months and show no signs of precipitation, loss of activity, color change or their ability to form microemulsions when additional water is mixed in.

To accomplish the processes of making a crystal clear, viscosity stable emulsion, the distilled or deionized water is added to the SQAC/essential oil or extract solution under moderate agitation. Depending upon the type of SQAC and essential oil or extract being used, the applicants did also discover that water heated above room temperature produces clear microemulsions more quickly. However, choosing a process water temperature depends in part on the boiling point of the SQAC/essential oil/polar solvent mixture being treated based on considerations.

The rate of water addition also has been found by the applicant to be dependent upon the components being used. Some systems allow water addition rates as rapid as less than one minute, while other systems require a water addition rate that will maintain a clear microemulsion mixing in the vessel. Microemulsion systems will maintain this clear appearance throughout the water addition process. This is one embodiment for carrying out the process of these inventions. If any turbidity of the mixing vessel contents occurs, there is a good chance a microemulsion will not be formed to completion resulting in less than crystal clarity of the final dispersion. Cloudy microemulsions may be repaired to form clear microemulsions by post heating the fully diluted microemulsion, then stopping the agitation and allowing the microemulsion to slowly cool to room temperature.

Although most of the aging stability studies were performed on economically shippable SQAC concentrations, further dilution with water produced crystal clear, stable microemulsions all the way down to application strength SQAC concentrations. Stability against precipitation remained excellent through this entire dilution range.

The present inventions can best be understood after a review of the following examples:

Example 1

Into an 8 oz. glass jar was weighed 16.67 g of Bioshield 7200 (72% active SQAC) followed by 3.60 g of tea tree essential oil and stirred on a magnetic stirring plate until two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of tea tree oil in a 6.0% active Bioshield continuous phase. Brookfield viscosity of the freshly prepared microemulsion was measured at 10 cPs at 25 C and the pH was measured 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 40 cPs and 5 Nephelos Turbidity Units (NTU).

Example 2

Into an 8 oz. glass jar was weighed 16.67 g of Bioshield 7200 (72% active SQAC) followed by 2.22 g of peppermint essential oil and stirred on a magnetic stirring plate until the two components were clear and uniform (~1 min) With continued moderate stirring, 181.11 g of distilled water at a temperature of 35 C to 45 C was rapidly poured into the jar. Stirring was continued as the transparent concentrate slowly dissolved in the water to form a crystal clear microemulsion of peppermint oil in a 6.0% active Bioshield continuous phase. Brookfield viscosity of the freshly prepared microemulsion was measured at 10 cPs at 25 C and the pH was measured 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 8 months aging at 25 C this sample was measured at 20 cPs and 33 NTU.

Example 3

Into an 8 oz. glass jar was weighed 16.67 g of Bioshield 7200 (72% active SQAC) followed by 2.18 g of Thyme essential oil (*T. vulgaris*) and stirred on a magnetic stirring plate until the two components were clear and uniform (~1 min) With continued moderate stirring, 181.15 g of distilled water at a temperature of 35 C to 45 C was rapidly poured into the jar. Stirring was continued as the transparent concentrate slowly dissolved in the water to foul' a crystal clear microemulsion of thyme oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 6 months aging at 25 C this sample was measured at 24 cPs and 30 NTU.

Example 4

Into an 8 oz. glass jar was weighed 16.67 g of Bioshield 7200 (72% active SQAC) followed by 3.60 g of grapefruit essential oil and stirred on a magnetic stirring plate until the two components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of grapefruit oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 12 cPs and 10 NTU.

Example 5

Into an 8 oz. glass jar was weighed 16.67 g of Bioshield 7200 (72% active SQAC) followed by 3.60 g of orange essential oil and stirred on a magnetic stirring plate until the two components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of orange oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 22 cPs and 5 NTU.

Example 6

Into an 8 oz. glass jar was weighed 16.67 g of Bioshield 7200 (72% active SQAC) followed by 3.60 g of lime essential oil and stirred on a magnetic stirring plate until the two components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of lime oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 32 cPs and 12 NTU.

Example 7

Into an 8 oz. glass jar was weighed 16.67 g of Bioshield 7200 (72% active SQAC) followed by 3.60 g of tangerine essential oil and stirred on a magnetic stirring plate until the two components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of tangerine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 16 cPs and 5 Nephelos Turbidity Units (NTU).

Example 8

Into an 8 oz. glass jar was weighed 16.67 g of Bioshield 7200 (72% active SQAC) followed by 3.60 g of lemon essential oil and stirred on a magnetic stirring plate until the two components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of lemon oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 16 cPs and 5 Nephelos Turbidity Units (NTU).

Example 9

Into an 8 oz. glass jar was weighed 16.67 g of Bioshield 7200 (72% active SQAC) followed by 3.60 g of pine essential oil and stirred on a magnetic stirring plate until the components were clear and uniform (~1 min) With continued moderate stirring, 179.73 g of distilled water at a temperature of 35 C to 45 C was rapidly poured into the jar. Stirring was continued as the transparent concentrate slowly dissolved in the water to form a crystal clear microemulsion of pine oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 18 cPs and 9 NTU.

Example 10

Into an 8 oz. glass jar was weighed 16.67 g of Bioshield 7200 (72% active SQAC) followed by 3.60 g of cedarwood essential oil and stirred on a magnetic stirring plate until the two components were clear and uniform (~1 min). With continued moderate stirring, 179.73 g of distilled water at a temperature of 35 C to 45 C was rapidly poured into the jar. Stirring was continued as the transparent concentrate slowly dissolved in the water to form a crystal clear microemulsion of cedarwood oil in a 6.0% active Bioshield continuous phase. Brookfield viscosity of the freshly prepared microemulsion was measured at 10 cPs at 25 C and the pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 4 cPs and 5 NTU.

Example 11

Into an 8 oz. glass jar was weighed 16.67 g of Bioshield 7200 (72% active SQAC) followed by 3.60 g of d-limonene (orange peel extract) and stirred on a magnetic stirring plate until the two components were clear and uniform (~1 min). With continued moderate stirring, 179.73 g of distilled water at a temperature of 35 C to 45 C was rapidly poured into the Stirring was continued as the transparent concentrate slowly dissolved in the water to form a crystal clear microemulsion of d-limonene oil in a 6.0% active Bioshield continuous phase. Brookfield viscosity of the freshly prepared microemulsion was measured at 10 cPs at 25 C and pH was measured at 3.7 without any adjustment. The jar was sealed and placed in a 25 C static oven and analyzed weekly for both viscosity increase (linear condensation polymerization) and development of insoluble precipitation (3 dimensional crosslinking) as measured by Hach Ratio Turbidimetry. After 3 months aging at 25 C this sample was measured at 18 cPs and 8 NTU. A further dilution of the stabilized 6% solution down to 0.75% active SQAC measured <1 NTU 3 months aging at 25 C.

Comparative Example 12

Into an 8 oz. glass jar was weighed 16.67 g of Bioshield 7200 (72% active SQAC) followed by NO essential oil or extract. With moderate stirring, 183.33 g of distilled water at a temperature of 35 C to 45 C was rapidly poured into the jar. Stirring was continued as the transparent concentrate slowly dissolved in the water to form a crystal clear solution of a 6.0% active Bioshield. Brookfield viscosity of the freshly prepared solution was measured at 10 cPs at 25 C and the pH was measured at 3.6 without any adjustment. The jar was sealed and placed in a 25 C static oven and analyzed daily for both viscosity increase (linear condensation polymerization) and development of insoluble precipitation (3 dimensional crosslinking) as measured by Hach Ratio Turbidimetry. After 13 days aging at 25 C this sample was measured at 630 cPs and 100 NTU, exceeding both storage stability limits set for these parameters.

A summary of findings of the Examples is set forth in TABLE 1:

TABLE 1

| | | | INITIAL | | | AFTER AGING | | |
|---|---|---|---|---|---|---|---|---|
| SQAC (g) | BOTANICAL | BOTANICAL (g) | WATER (g) | TURBIDITY (NTU) | VISCOSITY (cPs) | pH | TURBIDITY (NTU) | VISCOSITY (cPs) | AGE (months) |

EFFECT OF BOTANICALS ON TURBIDITY AND VISCOSITY OF AGED SQAC COMPOSITIONS

| SQAC (g) | BOTANICAL | BOTANICAL (g) | WATER (g) | TURBIDITY (NTU) | VISCOSITY (cPs) | pH | TURBIDITY (NTU) | VISCOSITY (cPs) | AGE (months) |
|---|---|---|---|---|---|---|---|---|---|
| 16.67 | Tea tree | 3.6 | 179.73 | 1 | 10 | 3.7 | 5 | 40 | 3 |
| 16.67 | Peppermint | 2.22 | 181.11 | 1 | 10 | 3.7 | 33 | 20 | 8 |
| 16.67 | Thyme | 2.18 | 181.15 | 1 | 10 | 3.7 | 30 | 24 | 6 |
| 16.67 | Grapefruit | 3.6 | 179.73 | 1 | 10 | 3.7 | 10 | 12 | 3 |
| 16.67 | Orange | 3.6 | 179.73 | 1 | 10 | 3.7 | 5 | 22 | 3 |
| 16.67 | lime | 3.6 | 179.73 | 1 | 10 | 3.7 | 12 | 32 | 3 |
| 16.67 | Tangerine | 3.6 | 179.73 | 1 | 10 | 3.7 | 5 | 16 | 3 |
| 16.67 | Lemon | 3.6 | 179.73 | 1 | 10 | 3.7 | 5 | 16 | 3 |
| 16.67 | Pine | 3.6 | 179.73 | 1 | 10 | 3.7 | 9 | 18 | 3 |
| 16.67 | Cedarwood | 3.6 | 179.73 | 1 | 10 | 3.7 | 5 | 4 | 3 |
| 16.67 | Orange Peel | 3.6 | 179.73 | 1 | 10 | 3.7 | 8 | 18 | 3 |
| 16.67 | NONE | 0 | 183.33 | 1 | 10 | 3.6 | 100 | 630 | 0.43 |

FIG. 1 graphically represents the overall desirability of microbial compositions as a function of the concentration of volatile botanical and the concentration of silanol quaternary ammonium compound. This is shown in the form of a surface response curve illustrating the interplay of the concentration of the SQAC and essential oil on the desirability of the composition, including turbidity, viscosity and stability. More specifically, compositions were rated 5 if they were expected to be "superior". Compositions were rated 4 if they were expected to be "good". Compositions were rated 3 if they were expected to be "acceptable". Compositions were rated 2 if they were expected to be "poor". Compositions were rated 1 if they were expected to be "unacceptable". As can be seen, there is a "sweet spot" for achieving the most desirable composition, as indicated by the 5's. Indeed even very low concentrations of antimicrobial SQAC's are beneficial.

This surface response curve is set forth on prophetic data of TABLE 2:

TABLE 2

| Wt % Volatile Botanical on Active SQAC | Desirability @ 0.75% Active SQAC | Desirability @ 6.0% Active SQAC |
|---|---|---|
| 0 | 1 | 1 |
| 5 | 1 | 1 |
| 10 | 2 | 2 |
| 15 | 5 | 3 |
| 20 | 5 | 4 |
| 25 | 5 | 5 |
| 30 | 5 | 5 |
| 35 | 3 | 2 |
| 40 | 1 | 1 |
| 50 | 1 | 1 |

Figure 2:
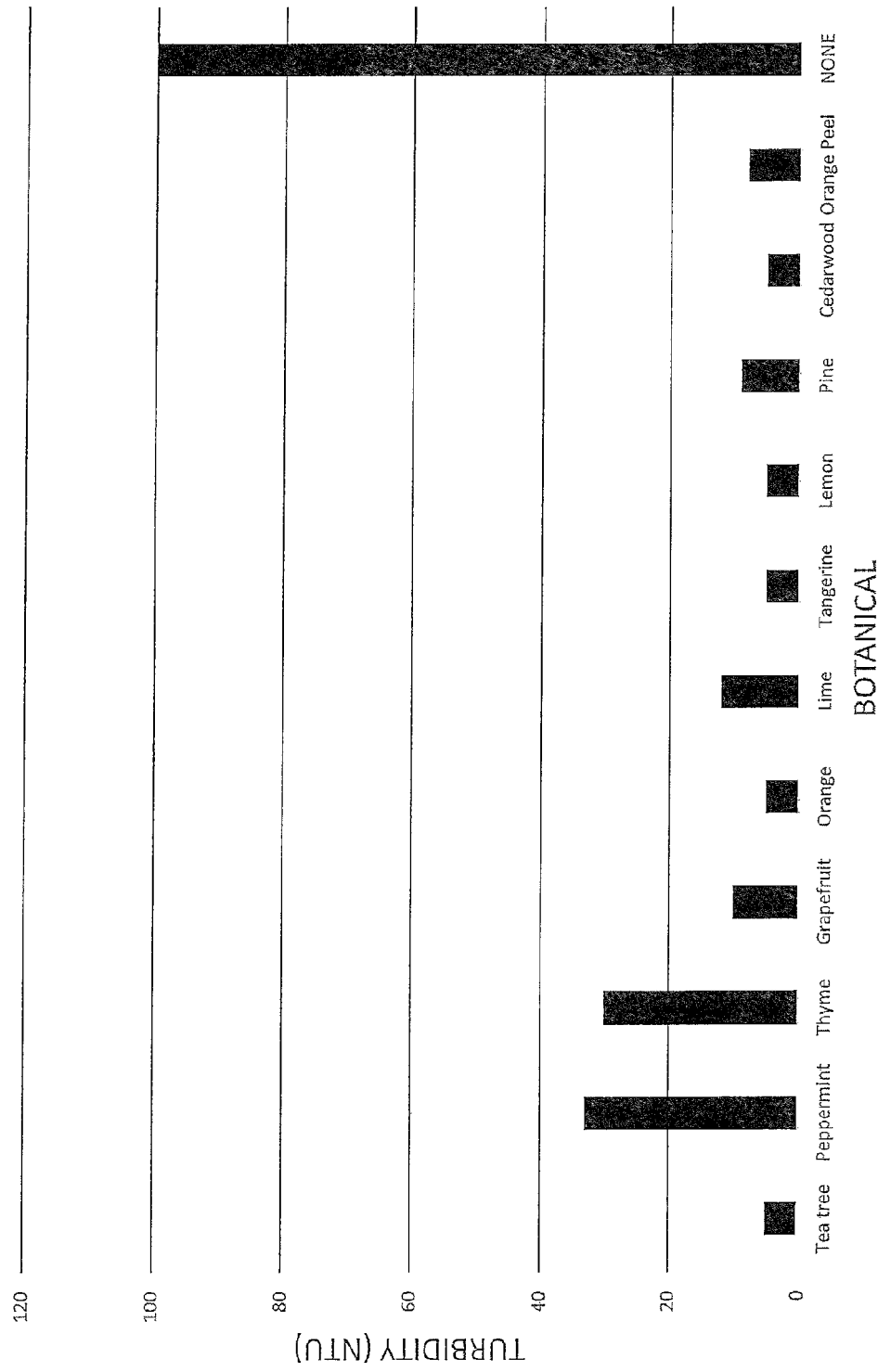
FIG. 2 illustrates the turbidity of various SQAC/botanical compositions compared to a composition having no botanical element.

As shown in FIG. 2, aged compositions having botanicals exhibit substantially lower turbidity than the aged composition having no botanicals. The data corresponding to this graph is set forth in TABLE 1. It is important to note that the negative control ("NONE") was aged only 13 days, while the test samples were aged 3-8 months.

Figure 3:
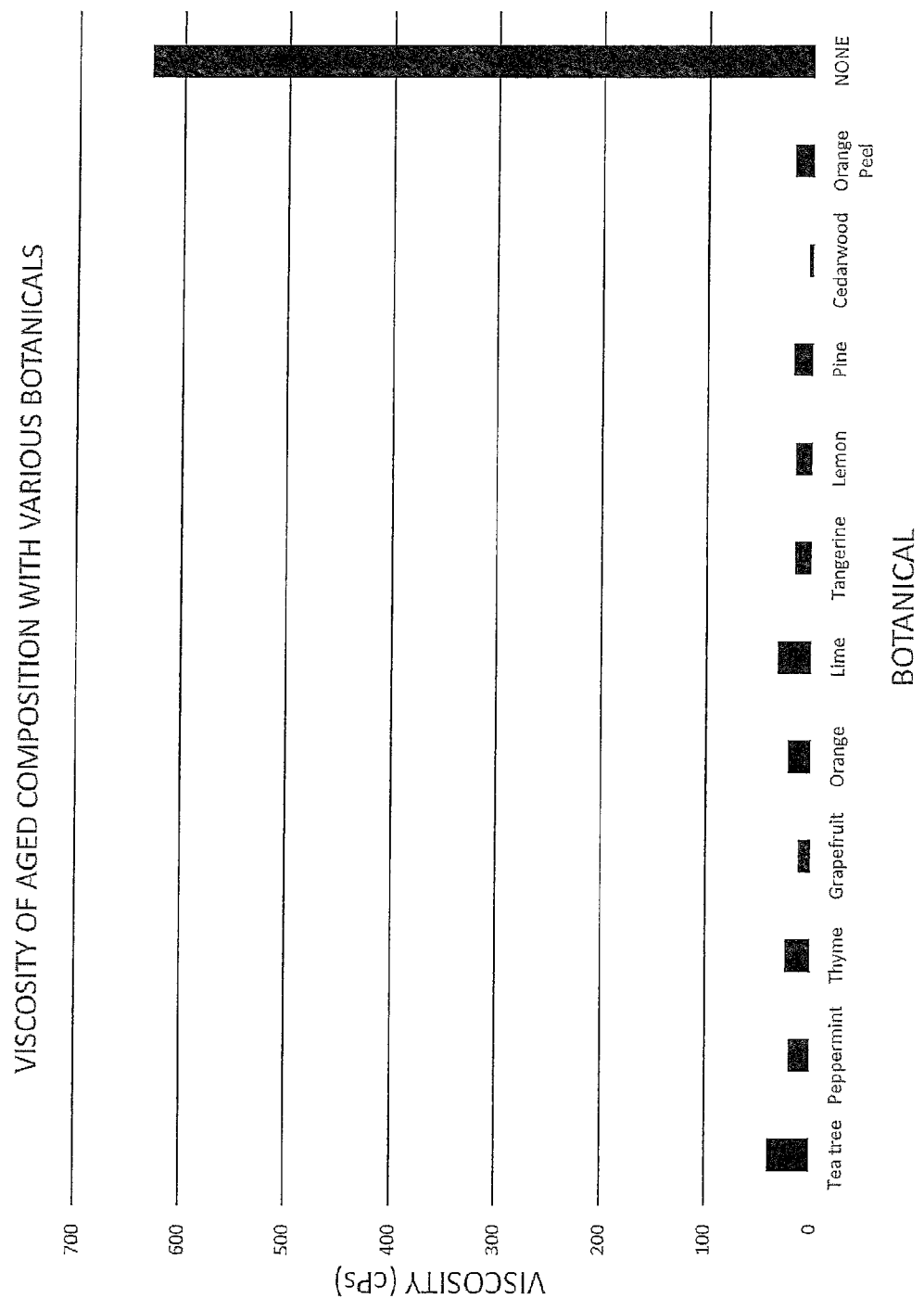
FIG. 3 illustrates the viscosity of various SQAC/botanical compositions compared to a composition having no botanical element.
Figure 4:
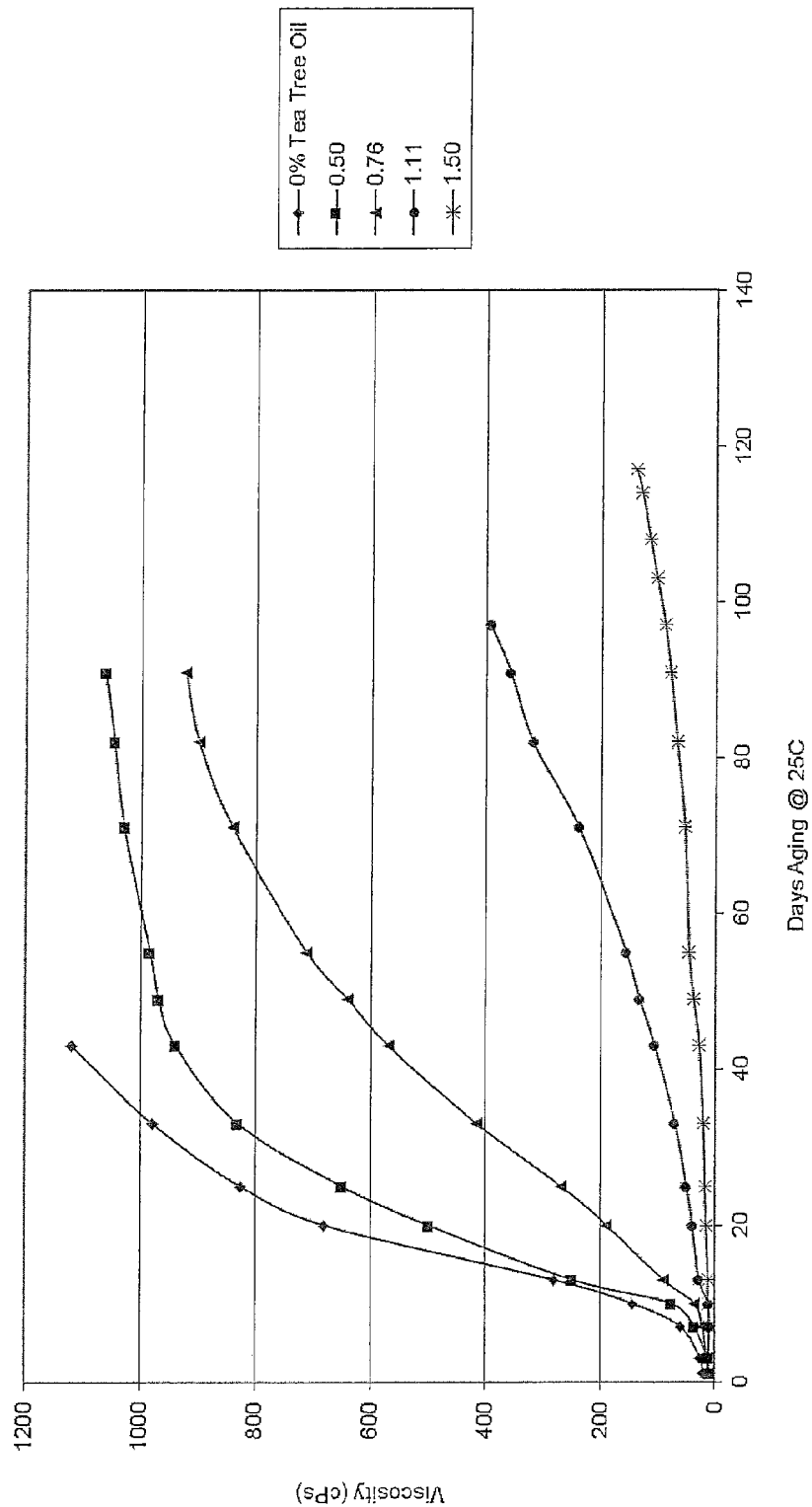
FIG. 4 demonstrates the viscosity of SQAC/Tea Tree Oil compositions over time compared to a composition having no Tea Tree Oil.
Figure 5:
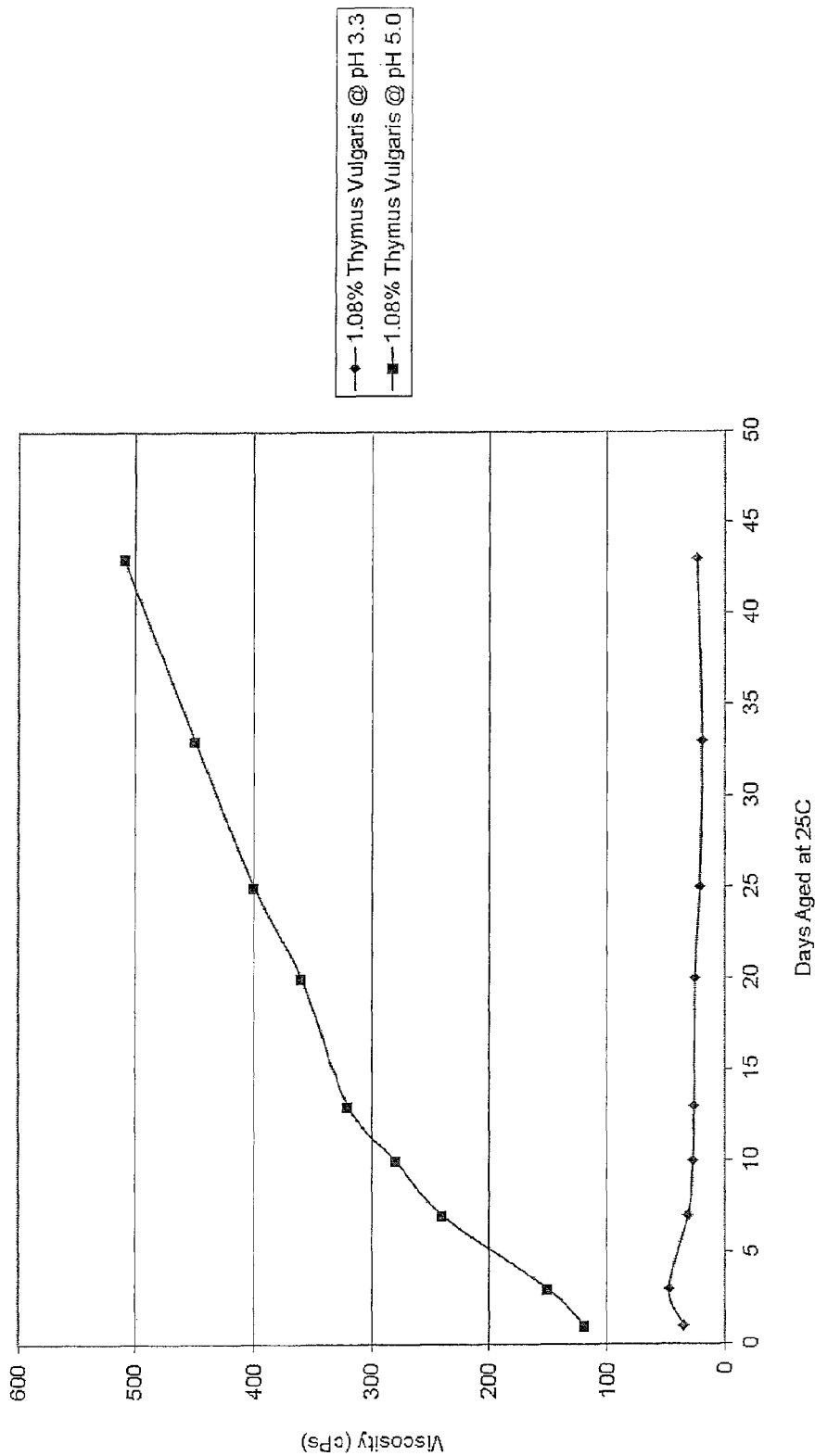
FIG. 5 demonstrates the viscosity of SQAC/Thyme Essential Oil compositions over time compared to a composition having no Thyme Essential Oil.

As shown in FIG. 3, aged compositions having botanicals exhibit substantially lower viscosity than the aged composition having no botanicals. The data corresponding to this graph is set forth in TABLE 1. It is important to note that the negative control ("NONE") was aged only 13 days, while the test samples were aged 1-8 months.

Figure 6:
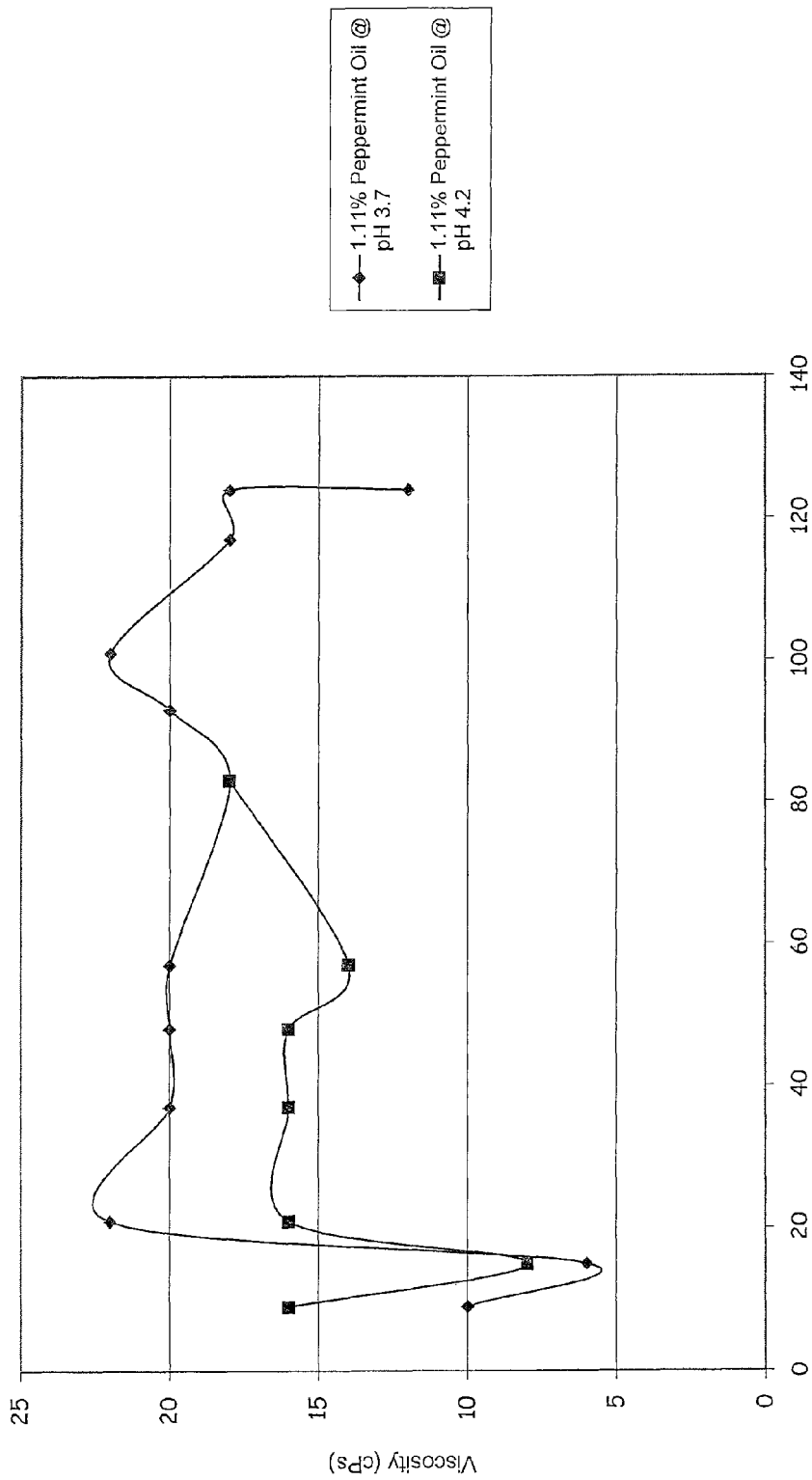
FIG. 6 demonstrates the viscosity of the same concentration of peppermint oil at two different pHs.
Figure 7:
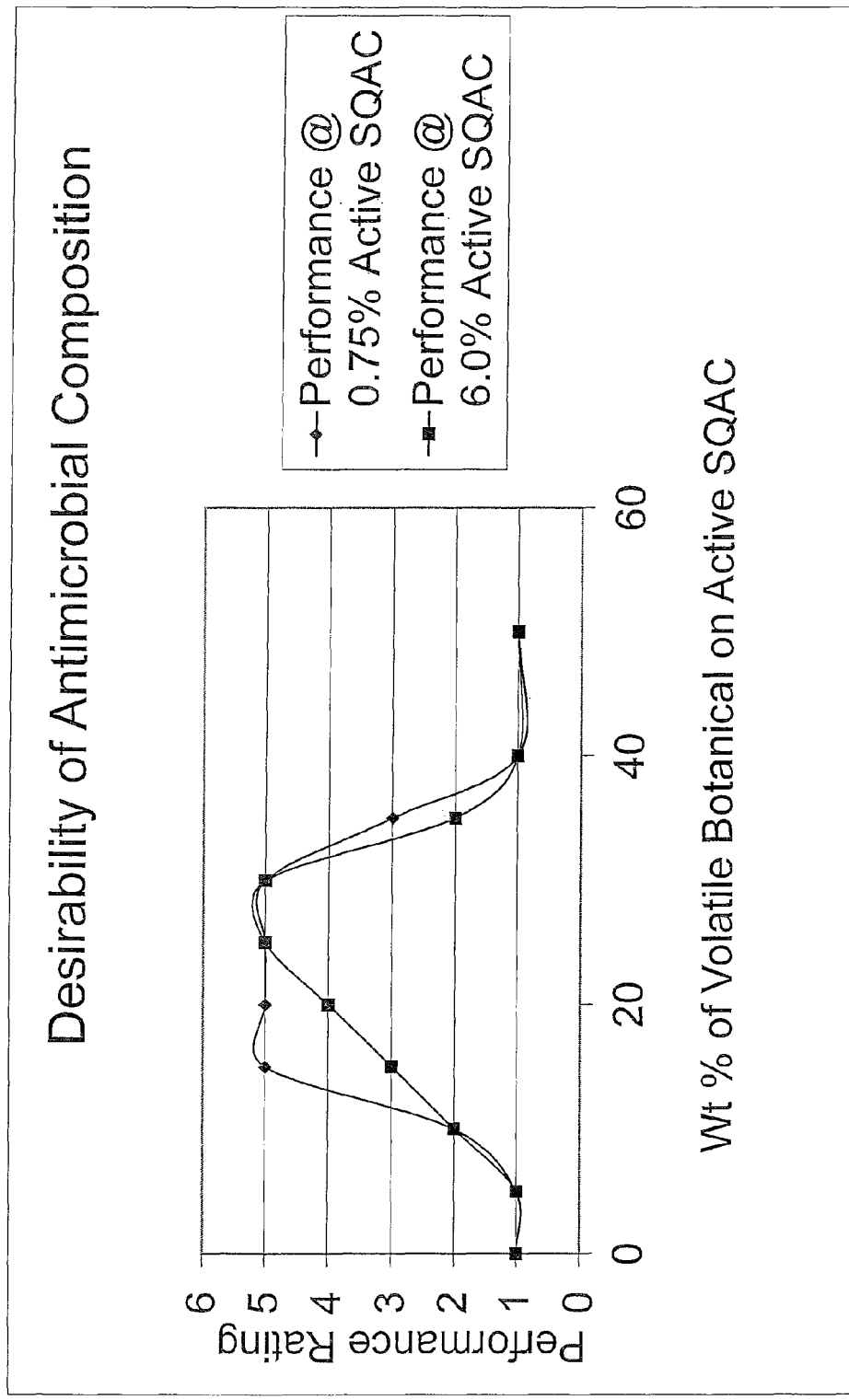
FIG. 7 depicts the aqueous stability of both a 0.75% and a 6.0% solution of SQAC as a function of ratio of volatile botanical to SQAC.

FIG. 6 depicts demonstrates the viscosity of the same concentration of peppermint oil at pH of 3.7 and 4.2. The 4.2 pH sample fully precipitated out after 80 days, so there was no viscosity or data charted after 80 days.

Compositions of the present invention can be applied to organic or inorganic substrates, an amount that is antimicrobial, or microbiostatic, for the specific article, by application methods including brushing, dipping, soaking, or spraying techniques. Substrates include: Air filters for furnaces, air-conditioners, air purification devices, automobiles, aquariums or recirculating air handling systems; materials associated with air filters; bed sheets, blankets, and bedspreads; buffer pads (abrasive and polishing); carpets and draperies; concrete additive for sewer pipes, manholes and concrete sewer structures; concrete additive for repair and renewal of sewer pipes and manholes and concrete sewer structures; fiberfill for upholstery, sleeping bags, apparel, the fiber is cotton, natural down, nylon, polyester, rayon, or wool; fiberglass ductboard; fire hose fabric; humidifier belts; mattress pads and ticking; underwear and outerwear including apparel such as jackets, sweaters, sweatshirts, coats, raincoats, overcoats, jerseys, ponchos; non-woven disposable diapers; non-woven polyester; polyurethane and cellulose foam for household, industrial, and institutional mops; polyurethane and polyethylene foam, when covered; polyurethane foam for packaging and cushioning in non-food contact applications; polyurethane foam used as a growth medium for non-food crops and plants; pre-moistened towelettes and wipes (these do not impart pesticidal properties; roofing materials such as shingles, roofing granules, wood shakes, felt, stone and synthetic overcoats; sand bags, tents, tarpaulins, sails and ropes; athletic and casual shoes; shoe insoles; shower curtains; socks comprised of nylon, nylon/orion, cotton/nylon, linen/LYCRA, acrylic/polypropylene/nylon/LYCRA, wool/silk/nylon/LYCRA and wool/acrylic/nylon/LYCRA; throw rugs; toweling made of 100 percent cotton, 100 percent polyester, and blends of the two fibers; toilet tank and seat covers; umbrellas; upholstery made of acetates, acrylics, cotton, fiberglass, nylon, polyester, polyolefins, polypropylene, rayon, SPANDEX, vinyl, and wool; vacuum cleaner bags and filters; vinyl paper-wallpaper for non-food contact surfaces; disposable wiping cloths that can be used multiple purposes such as dusting or washing furniture, cars, walls, windows, floors, appliances, dishes, counter tops; the wiping cloths do not impart pesticide properties; women's hosiery, and women's intimate apparel.

Exemplary articles that are within the scope of the disclosed inventions, and the method of practicing the invention include:

Sample Article 1:

In Sample Article 1 the antimicrobial mixture may be used for odor causing bacteria, bacteria which cause staining and discoloration, and fungi (mold and mildew). Suitable articles include bedsheets, blankets, bedspreads, curtains, draperies (washable only), underwear, socks, intimate apparel, hosiery, throw rugs, toweling, toilet tank covers, shower curtains, shoe insoles, outerwear apparel (jackets, sweaters, sweatshirts, coats, raincoats, overcoats, jerseys, ponchos). The composition can be applied to fabrics made of acetates, acrylics, cotton, fiberglass, linen, Lycra, nylon, orion, polyester, polyethylene, polyolefins, polypropylene, rayon, silk, spandex, vinyl, and wool.

Methods of application include:

DIP/SOAK: Use appropriate sized wash basin or tub for dipping/soaking the item you are treating. Use enough composition to completely submerge item. Keep item in solution for 3 minutes. Remove item and wring excess liquid. Drying may be attained by dripping dry or wringing excess liquid from treated item. For larger items (e.g., bedspreads, curtains, draperies), place in washing machine on spin cycle to aid in the removal of excess liquid. Test staining and color-fastness of fabric and carpets by treating and drying a small concealed area prior to application. Do not reuse solution after dipping/soaking. Dry treated articles before use. Substrates can be hang-dried at room temperature or at temperatures to a maximum of 160° C. (320° F.), (for example in a clothes dryer). Remove excess liquid before attempting to dry in a clothes dryer. If necessary, reapply the composition every three months or when odor, staining and discoloration due to bacteria, mold stains, and mildew stains return.

SPRAY: Clean surface prior to application. Using a trigger pump sprayer or pressure sprayer, spray the entire surface area 4"-6" from the surface making sure the surface is completely covered. Let stand until dry or let stand 3 minutes and wipe dry with cloth or sponge. If spotting occurs, wipe with moist cloth or sponge. Test staining and color-fastness of fabric by treating and drying a small, concealed area prior to application. If necessary, reapply the composition every three months or when odor, staining and discoloration due to bacteria, mold stains and mildew stains return.

Sample Article 2:

In Sample Article 2 the antimicrobial mixture may be used for odor causing bacteria, bacteria which cause staining and discoloration, and fungi (mold and mildew), and algae.

Suitable substrates include air filters and air filter material for furnaces, air conditioners, air purification systems, automobiles, recirculating air handling systems, vacuum cleaner filters, and aquariums.

Methods of application include:

SPRAY: When treating filters, remove filter from the unit. Using a trigger pump sprayer or pressure sprayer, spray the entire surface area 4"-6" from the surface making sure the surface is completely covered. Apply and then let stand until dry. If necessary, reapply the composition every three months or when odor, staining and discoloration due to bacteria, mold stains, mildew stains and algae stains return.

Sample Article 3:

In Sample Article 3 the antimicrobial mixture may be used for odor causing bacteria, bacteria which cause staining and discoloration, and fungi (mold and mildew). Suitable articles include carpeting.

Methods of application include:

SPRAY: Apply to clean carpet surface. Using a trigger pump sprayer or pressure sprayer, spray the entire surface area 4"-6" from the surface making sure the surface is completely covered. For rotary jet extraction cleaners and carpet steamers, add the composition directly to the cleaning tank, then operate the equipment in accordance with manufacturer's instructions. Apply and then let stand until dry. Test staining and color-fastness of carpets by treating and drying a small, concealed area prior to application. The composition treats approximately 200 square feet per gallon (50 square feet per quart). When treating coarser substrates (e.g. wool carpeting), more composition may be required due to absorption. Dry carpet areas and surfaces before re-entry. A fan may be used to assist in drying carpeting. Remove children and pets from treated areas until completely dried. If necessary, reapply the composition every three months or when odor, staining and discoloration due to bacteria, mold stains and mildew stains return.

Sample Article 4,

In Sample Article 4 the antimicrobial mixture may be used for odor causing bacteria, bacteria which cause staining and discoloration, and fungi (mold and mildew).

Suitable articles include mattress pad and mattress ticking and upholstery composed of acetates, acrylics, cotton, fiberglass, nylon, polyester, polyethylene, polyolefins, polypropylene, rayon, spandex, vinyl, wool; fiberfill to be used in upholstery, sleeping bags, apparel, where the fiber is cotton, natural down, nylon, rayon or wool.

Methods of application include:

SPRAY: Clean surfaces prior to application. Using a trigger pump sprayer, spray the entire surface area 4"-6" from the surface making sure the surface is completely covered. Apply and then let stand until dry or let stand 3 minutes and wipe dry with cloth or sponge. If spotting occurs, wipe with moist cloth or sponge. Test staining and color-fastness of fabric by treating and drying a small, concealed area prior to application. When applying to mattress pads and ticking do not soak. Remove children and pets from treated area until completely dried. If necessary, reapply the composition every three months or when odor, staining and discoloration due to bacteria, mold stains and mildew stains return.

Sample Article 5:

In Sample Article 5 the antimicrobial mixture may be used for odor causing bacteria, bacteria which cause staining and discoloration, fungi (mold and mildew) and algae.

Suitable articles include tents, tarpaulins, sails, and ropes.

Methods of application include:

SPRAY: Clean surface prior to application. Using a trigger pump sprayer or pressure sprayer, spray the entire surface area 4"-6" from the surface making sure the surface is completely covered. Let stand until dry or let stand 3 minutes and wipe dry with cloth or sponge. If spotting occurs, wipe with moist cloth or sponge. Test staining and color-fastness of fabric by treating and drying a small, concealed area prior to application. If necessary, reapply the composition every three months or when odor, staining and discoloration due to bacteria, mold stains, mildew stains and algae stains return.

DIP/SOAK: Use appropriate sized wash basin or tub for dipping/soaking the item you are treating. Use enough composition to completely submerge item. Keep item in solution for three minutes. Remove item and wring excess liquid. Do not reuse solution after dipping/soaking. Dry treated articles before use. Substrates can be hang-dried at room temperature or at temperatures to a maximum of 160°

C. (320° F.); (for example in a clothes dryer). Remove excess liquid before attempting to dry in a clothes dryer. If necessary, reapply the composition every three months or when odor, staining and discoloration due to bacteria, mold stains, mildew stains, and algae stains return.

Sample Article 6:

In Sample Article 6 the antimicrobial mixture may be used for odor causing bacteria, bacteria which cause staining and discoloration, fungi (mold and mildew) and algae.

Suitable articles include roofing materials (such as shingles, roofing granules, wood shakes, felt, stone, synthetic overcoats).

Methods of application include:

SPRAY: Make sure the roof is clean prior to application. Using a pressure sprayer, spray the entire surface area 6"-12" from the surface making sure the surface is completely covered. After applying the composition, let stand until dry. The composition treats approximately 200 square feet of roofing per gallon (50 square feet per quart). If necessary, reapply the composition every three months or when odor, staining and discoloration due to bacteria, mold stains, mildew stains, and algae stains return.

Sample Article 7:

In Sample Article 7 the antimicrobial mixture may be used for odor causing bacteria, bacteria which cause staining and discoloration, and fungi (mold and mildew).

Suitable articles include buffer pads (polishing and abrasive), polyurethane and cellulose foam for household mops, vacuum cleaner bags, umbrellas, casual shoes, athletic shoes.

Methods of application include:

SPRAY: Clean surface prior to application. Using a trigger pump sprayer or pressure sprayer, spray the entire surface area 4"-6" from the surface making sure the surface is completely covered. Let stand until dry or let stand 3 minutes and wipe dry with cloth or sponge. If spotting occurs, wipe with moist cloth or sponge. If necessary, reapply the composition every three months or when odor, staining and discoloration due to bacteria, mold stains and mildew stains return.

Sample Article 8:

In Sample Article 8 the antimicrobial mixture may be used for odor causing bacteria, bacteria which cause staining and discoloration, and fungi (mold and mildew).

Suitable articles include tubs, glazed tiles, vanity tops, shower curtains, shower stalls (areas), sinks, washable walls, wall paper for non-food contact, floors, window sills, cabinets, garbage cans, appliances, refrigerators (exterior), fiberglass, formica, glazed tiles, glazed porcelain, synthetic marble, plastic, vinyl.

Methods of application include:

SPRAY: Using a trigger pump sprayer, spray the entire surface area 4"-6" from the surface making sure the surface is completely covered. Let stand until dry or let stand 3 minutes and wipe dry with cloth or sponge. If spotting occurs, wipe with moist cloth or sponge. If necessary, reapply the composition every three months or when odor, staining and discoloration due to bacteria, mold stains, and mildew stains return.

Sample Article 9:

In Sample Article 9 the antimicrobial mixture may be used for fungi (including mold and mildew) and algae which cause odors, staining and discoloration as a static agent.

Suitable articles include building materials and components (metal, plastic, concrete): siding, wallboard, insulation, concrete and concrete products, cinder blocks, brick, stone, ceiling tiles, architectural metal, louvers, vents, coping.

Methods of application include:

ADDITIVE: This composition may be used in materials that are incorporated into manufactured products at the point of manufacturing, as in the manufacture of wallboard, concrete, and masonry (cinder) block building materials to inhibit and prevent the growth of mold organisms when the materials are subjected to moist or wet environments.

In concrete products, the composition may be used as a concrete additive added directly during concrete preparation. Use 16 fluid ounces of the composition per cubic yard (approx 0.2% active by weight or water) of concrete. Add to water before addition of concrete. Addition of the composition reduces deterioration of sewer pipes and manholes by inhibiting microbiologically inducted corrosion. This composition can be used as a concrete additive for repair and renewal of sewer pipes and manholes and concrete sewer structures. Do not use in treatment of storm drains.

BRUSH, DIP/SOAK, SPRAY:

In metal products, the composition is not to be used for treatment of in place heating, ventilation, air conditioning, and refrigeration systems surfaces such as louvers, vents and ducts. Dilute 16 ounces of the composition per gallon of water (0.625% active); mix well. Apply by brushing, dipping, soaking or spraying techniques and then let stand until dry or let stand 3 minutes and wipe dry with cloth and sponge. If spotting occurs, wipe with moist cloth or sponge. The composition treats approximately 200 square feet per diluted gallon of water'.

As a preventative treatment, to inhibit surface mold and mildew growth on wood, wallboard, concrete, and masonry (cinder) block construction material. Mix the composition into water at the rate of 1 gallon (10.5 lb.) per 50 gallons of water and apply evenly by paintbrush, airless sprayer, low pressure hand wand, or backpack sprayer. Assure uniform coverage of surfaces to be protected (approximately 500 sf per gallon). Surfaces should be evenly wet without runoff or pooling. Let surfaces dry thoroughly before applying additional coatings. Before applying this product, visible mold growth must be removed and conditions favorable to mold growth must be identified and corrected.

Sample Article 10:

In Sample Article 10 the antimicrobial mixture may be used for fungi (including mold and mildew) and algae which cause odors, staining and discoloration as a static agent.

Suitable articles include roofing materials: shingles, roofing granules, tiles, membranes, underlayment, wood shakes, felt, stone, concrete, synthetic overcoats.

Methods of application include:

ADDITIVE: This composition may be used in materials that are incorporated into manufactured products at the point of manufacturing.

Sample Article 11:

In Sample Article 11 the antimicrobial mixture may be used for fungi (including mold and mildew) and algae which cause odors, staining and discoloration as a static agent.

Suitable articles include walls and flooring: vinyl, wood, laminate, concrete, tile, stone, wallboard, plaster, dryvit concrete, cinder block, brick, wall paper and wall coverings, carpet, underlayment, mats.

Methods of application include:

ADDITIVE: This composition may be used in materials that are incorporated into manufactured products at the point of manufacturing.

DIP/SOAK: Dilute 8 ounces of the composition per gallon of water (2 oz. per quart; 1 oz. per pint); mix well. Completely submerge item in solution for 3 minutes. Remove item and dry. Test for staining and colorfastness of fabrics by treating and drying a small, concealed area prior to application. Do no reuse solution after dipping/soaking.

SPRAY: Dilute 8 ounces of composition per gallon of water (2 oz. per quart; 1 oz. per pint); mix well. Apply and then let stand until dry or let stand 3 minutes and wipe dry with cloth or sponge. If spotting occurs, wipe with moist cloth or sponge. Test for staining and colorfastness of fabrics and carpets by treating and drying a small, concealed area prior to application. This composition treats approximately 200 square feet per diluted gallon of water. When treating coarser substrates, more composition may be required due to absorption. Dry articles in accordance with standard manufacturing drying procedures. A fan may be used to assist in drying carpeting. The substrate can be dried at room temperature or at temperatures to a maximum of 160° C. (320° F.), or industry standards for drying.

Sample Article 12:

In Sample Article 12 the antimicrobial mixture may be used for fungi (including mold and mildew) and algae which cause odors, staining and discoloration as a static agent.

Suitable articles include fibers and fabrics (natural and synthetic, woven and non-woven): acetates, acrylics, cotton, nylon, LYCRA, polyester, polyethylene, polyolefins, polypropylene, rayon, SPANDEX, vinyl, wool, orion, silk and blends of these fibers and natural down. Types of finished products are: Apparel including recreational gear, sportswear, sleepwear, sock, hosiery, undergarments, gloves, uniform, footwear (boots, shoes and components) shoe insoles, athletic and casual shoes; Outwear (jackets, sweaters, sweatshirts, coats, raincoats, overcoats, jerseys, ponchos) bedspreads, blankets, sheets, pillow covers, quilts, pillows, mattress pad, ticking, filling, sleeping bags; Upholstery, curtains, drapery, mats, throw rugs, furniture, vinyl, toweling, awning, tents, tarpaulin, sails, rope and other outdoor equipment, umbrellas.

Methods of application include:

ADDITIVE: This composition may be used in materials that are incorporated into manufactured products at the point of manufacturing. The composition may be used in formulation microbiostats for use in laundry additives, carpet treatment products, and upholstery and drapery treatment products.

SPRAY: Dilute 8 ounces of the composition per gallon of water (2 oz. per quart; 1 oz. per pint); mix well. Apply and then let stand until dry or let stand 3 minutes and wipe dry with cloth or sponge. If spotting occurs, wipe with moist cloth or sponge. Test for staining and colorfastness of fabrics and carpets by treating and drying a small, concealed area prior to application. The composition treats approximately 200 square feet per diluted gallon of water. When treating coarser substrates, more composition may be required due to absorption. Dry articles in accordance with standard manufacturing drying procedures. A fan may be used to assist in drying carpeting.

DIP/SOAK: Dilute 8 ounces of composition per gallon of water (2 oz. per quart; 1 oz. per pint); mix well. Completely submerge item in solution for 3 minutes. Remove item and dry. Test for staining and colorfastness of fabrics by treating and drying a small, concealed area prior to application. Do no reuse solution after dipping/soaking. The substrate can be dried at room temperatures or at temperatures to a maximum of 160° C. (320° F.), or industry standards for drying.

Sample Article 13:

In Sample Article 13 the antimicrobial mixture may be used for fungi (including mold and mildew) and algae which cause odors, staining and discoloration as a static agent.

Suitable articles include paints and coating: latex indoor/outdoor paints and stains, woodstains, architectural paints, lacquer and maintenance coatings, films, laminates and finishes including alkyd, urethane, enamel, epoxy, siloxaline, amino resins, textile coatings, extrusion coatings, architectural coatings and overlays, anti-corrosion coatings, fire-resistant coatings, aliphatic coatings, vinyl ester and polyester coatings, gel coatings, amino resins, resins used as additive mixes for cement, epoxy laminating resins, and blends and copolymers thereof.

Methods of application include:

ADDITIVE: The composition can be used in paints and coatings as an in can preservative for protection of paint film and coating film. Incorporate this product into coating that are intended for end use applications. The purpose of the coating is to seal the end product from moisture and corrosion. The purpose of the composition in the coating as an in can preservative is to inhibit the growth of mold, mildew, fungus and bacteria that cause odor, discolorations, staining, deterioration or corrosion on the surface of the coating film. The product protects the applied coating itself from microorganism attack, not the underlying substrate. This product is not intended for remediation, prevention or control of existing or anticipated public health related microorganism.

PANTS AND COATINGS: Disperse 100.9 lb to 151.35 pounds (100.9 lb=100.9 lb/1,009 lb.×5% active of composition=0.5% active) of composition per 100 gallons (1,009 lbs 100 gal. Specific Gravity=1.2) of exterior paint to obtain effective mildew control in the paint film after it is it applied. Use the high rate in areas favorable to mildew and mold growth, such where painted surfaces frequently are warm and moist. Disperse 151.35 pounds (151.35 lb=151.35 lbs/1,009 lb.×5% active of composition=0.75% active) of composition per 100 gallons (1,009 lbs=100 gal. Specific Gravity=1.2) when added to stains designed for exterior wood, protects the wood from surface molds and mildew stains cause by fungi. Disperse 100.9 lb to 151.35 pounds (100.9 lb=100.9 lb/1,009 lb.×5% active of composition=0.5% active) of composition per 100 gallons (1,009 lbs=100 gal. Specific Gravity=1.2) of interior latex paint. Composition can be used with either unmodified or alkyd modified acrylic, vinyl acrylic, or polyvinyl acetate latexes.

The composition can be added into the paint formula during the pigment grind operation, during or after letdown. DO NOT use in paints designed for applications on food-contact surfaces.

AQUEOUS ADHESIVES COATINGS: The composition may be incorporated into adhesives to protect the applied adhesive films from mold growth and decomposition. Fully disperse 100 pounds to 150 pounds (100 lb=100 lb/1,000 lb×5% active of composition=0.5% active) of composition per 1,000 pounds of adhesive while it is being manufactured. Use the high rate in areas favorable to mildew to mold growth, such as where surfaces frequently are warm and moist. DO NOT use in adhesives designed for applications on food-contact surfaces, or on the interior of buildings engaged in food processing or food handling.

AQUEOUS CAULKS AND SEALANT COATINGS: To provide mildew and mold control on caulking or sealing deposits after application, fully disperse 100 pounds to 150 pounds (100 lb=100 lb/1,000 lb×5% active of composition=0.5% active) of composition per 1,000 pounds of caulk or sealant products while they are being manufactured. The high rate is recommended for exterior caulks. DO NOT use in caulks or sealants designed for applications on food-contact surfaces.

DIP/SOAK: Dilute 8 ounces of composition per gallon of water (2 oz. per quart; 1 oz. per pint); mix well. Completely submerge item in solution for 3 minutes. Remove item and dry. Test for staining and colorfastness of fabrics by treating and drying a small, concealed area prior to application. Do no reuse solution after dipping/soaking.

Sample Article 14:

In Sample Article 14 the antimicrobial mixture may be used for fungi (including mold and mildew) and algae which cause odors, staining and discoloration as a static agent.

Suitable articles include miscellaneous items, including: polyurethane and cellulose foam for household, industrial and institutional mop, polyurethane and polyethylene foam, when covered, polyurethane foam for packaging and cushioning in non-food contact applications, polyurethane foam used as a growth medium for non-food crops and plants, premoistened towelettes and tissue wipes (these do not impart pesticidal properties), vacuum cleaner bags and filters, sponges and mops, disposable polyurethane foam cushions for Lapidus Airfloat Systems, non-woven disposable diapers, foam for packing and cushioning in non-food contact applications, conveyor and humidifier belts, buffer pads (abrasive and polishing), bathroom and nonfood contact kitchen hardware, air filters to be installed in furnaces; air conditioners, air purification devices, automobiles and recirculating air handling systems. Disposable wiping cloths that can be used for multiple purposes such as dusting or washing furniture, cars, walls, windows, floors, appliances, dishes, counter tops; these do not impart pesticidal properties.

Methods of application include:

ADDITIVE: This composition may be used in materials that are incorporated into manufactured products at the point of manufacturing.

DIP/SOAK: Dilute 8 ounces of composition per gallon of water (2 oz. per quart; 1 oz. per pint); mix well. Completely submerge item in solution for 3 minutes. Remove item and dry. Test for staining and colorfastness of fabrics by treating and drying a small, concealed area prior to application. Do not reuse solution after dipping/soaking.

Certain modifications and improvements will occur to those skilled in the art upon a reading of the foregoing description. By way of example, while in one embodiment, the compositions of the present inventions are synthesized using methanol as the volatile reaction medium, it is possible to subsequently remove the methanol and either replace it with another solvent, or yield a dry product. The dry product would yield up to approximately 99%, versus the 72% SQAC, generally disclosed herein. It should also be understood that, like any volatile compound, the volatile reaction mediums used herein will substantially dissipate, and therefore only a residual amount may be found in the end product. It should be understood that all such modifications and improvements have been deleted herein for the sake of conciseness and readability but are properly within the scope of the following claims. All ranges set forth herein include the endpoints and all increments there between, however small. Also, unless indicated otherwise or impossible, "approximately" and the like is +/−10%. It should be understood that all such modifications and improvements have been deleted herein for the sake of conciseness and readability but are properly within the scope of the following claims.

We claim:

1. A method of stabilizing an aqueous solution of SQAC from premature polymerization comprising:
   mixing an anhydrous SQAC defined as 3-(trimethoxysilyl) propyl-N-octadecyl-N,N-dimethyl ammonium chloride and an essential oil selected from the group consisting of grapefruit, lemon, lime, tangerine, orange, and mixtures thereof, to form a mixture,
   diluting the mixture to a desired aqueous concentration with demineralized water, and
   producing a stable and clear oil-in-water microemulsion that provides long-term stabilization from unwanted polymerization.

2. The method of claim 1 wherein the step of diluting the mixture with demineralized water further comprises diluting the mixture with a volume of water sufficient to produce an oil-in-water microemulsion containing six to ten percent (6-10%) by weight anhydrous SQAC.

3. The method of claim 1 wherein the step of diluting the mixture with demineralized water further comprises diluting the mixture with a volume of water sufficient to produce an oil-in-water microemulsion containing a tenth to six percent (0.1-6.0%) SQAC by weight.

4. The method of claim 1 wherein the step of mixing SQAC with the essential oil further includes defining a weight of the essential oil as five to forty percent (5-40%) by weight when compared to a weight of SQAC included in the mixture.

5. The method of claim 1 wherein the step of mixing SQAC with the essential oil further includes defining a weight of the essential oil as twenty-five to thirty-five percent (25-35%) by weight when compared to a weight (wt/wt) of SQAC present in the mixture.

6. The method of claim 1 wherein the step of producing an oil-in-water microemulsion further comprises producing a stable and clear oil-in-water microemulsion with six percent (6%) SQAC by weight and one and four fifths percent (1.8%) the essential oil by weight, that provides long-term stabilization from unwanted polymerization.

7. The method of claim 6 wherein long-term stabilization is defined as three years at twenty-five degrees Centigrade (25° C.) without viscosity increase or precipitation.

* * * * *